United States Patent [19]

Šušković et al.

[11] Patent Number: 5,559,251

[45] Date of Patent: Sep. 24, 1996

[54] DERIVATIVES OF AMINO-ASCORBIC ACID, THE PROCESSES FOR THEIR PREPARATION AND USE

[75] Inventors: Božidar Šušković; Vanja Vela; Mira Bunčić, all of Zagreb, Croatia

[73] Assignee: Pliva, farmaceutska, Croatia

[21] Appl. No.: 190,921

[22] Filed: Feb. 3, 1994

[30] Foreign Application Priority Data

Feb. 5, 1993 [HR] Croatia ............... 38103/93010366

[51] Int. Cl.⁶ .................................. C07D 305/12
[52] U.S. Cl. ......................................... 549/315
[58] Field of Search ................. 514/471, 474; 549/315

[56] References Cited

FOREIGN PATENT DOCUMENTS

| 0096930 | 12/1983 | European Pat. Off. . |
| 0096933 | 12/1983 | European Pat. Off. . |
| 0446539A1 | 9/1991 | European Pat. Off. . |
| 2616351 | 12/1976 | Germany . |

OTHER PUBLICATIONS

Abstract 65658z, Chemical Abstracts, vol. 117, No. 7 (1992).
Chemiker–Zeitung, vol. 109, No. 9 (1985), Heidelberg De pp. 277–280.
Abstract 6058y, Chemical Abstracts, vol. 113, No. 1 (1990).
March, Advanced Organic Chemistry, Reactions, Mechanisms, and Structure, Third Edition, John Wiley & Sons, Inc., New York, pp. 798–800 (1977).

*Primary Examiner*—C. Warren Ivy
*Assistant Examiner*—Amelia Owens
*Attorney, Agent, or Firm*—Pollock, Vande Sande & Priddy

[57] ABSTRACT

The invention relates to the process for the preparation of new derivatives of amino-ascorbic acid, their acid and alkali salts, processes for preparation and action.

According to this invention derivatives of amino-ascorbic acid are prepared by three types of reactions: 1. reductive alkylation of amino-ascorbic acid; 2. alkylation of primary and secondary amines with halogen-ascorbic acid and 3. acylation of amino-ascorbic acid.

5 Claims, 1 Drawing Sheet

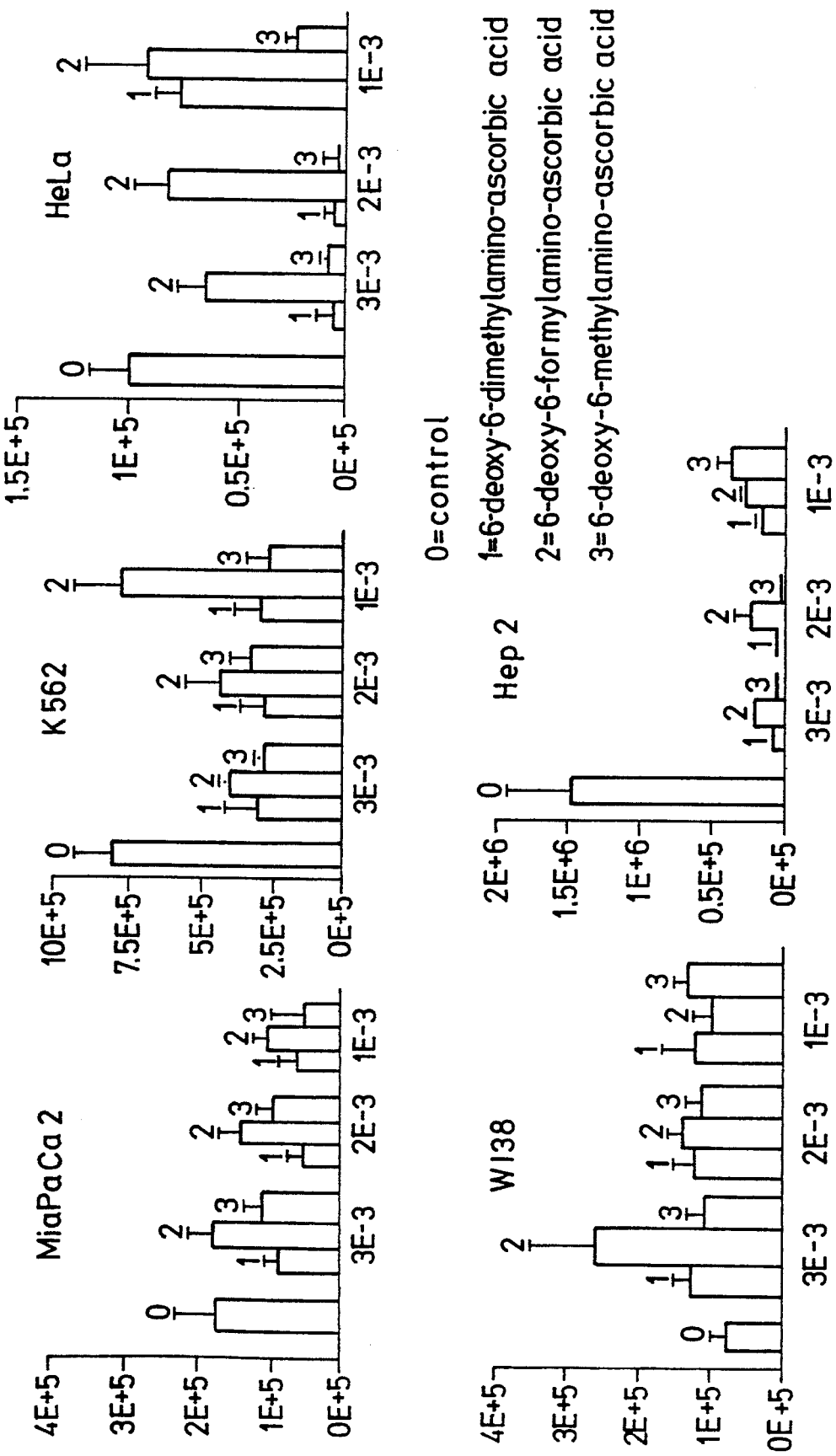

DERIVATIVES OF AMINO-ASCORBIC ACID, THE PROCESSES FOR THEIR PREPARATION AND USE

In continuation of our works on the preparation of the derivatives of ascorbic acid in the position $C_6$/Yug. pat. Application P-1852/88, Croat. Chim. Acta 62 (3), 537–544 (1989)/, and the studies of the relations between the structure/Acta Cryst. C45, 269–273 (1989), Croat. Chem. Acta 64 (3) (1991)/and biological activity (Re. Exp. Med. 190, 443–449 (1990)/, prepared were new derivatives of 6-deoxy-6-amino-ascorbic acid.

The present invention relates to new derivatives of amino-ascorbic acid of the general formula (I)

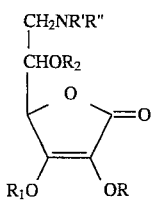
I wherein $R'$=H, $C_1$–$C_{18}$ alkyl atoms, $C_6$ cycloalkyl atoms, $C_6$–$C_{12}$ aryl atoms, heteroyl atoms, which represents a heterocyclic compound containing in the ring oxygen, sulfur or nitrogen as heteroatom, $R''$=$C_1$–$C_{18}$ alkyl atoms, $C_6$ cycloalkyl atoms, $C_6$–$C_{12}$ aryl atoms, heteroyl atoms, which represents a heterocyclic compound containing in the ring oxygen, sulfur or nitrogen as heteroatom, $R'R''$=$(CH_2R_3)_2$ wherein $R_3$=$C_1$–$C_{18}$ alkyl atoms, $C_6$ cycloalkyl atoms, $C_6$–$C_{12}$ aryl atoms, heteroylatoms, representing a heterocyclic compound containing in the ring oxygen, sulfur or nitrogen as heteroatom, i.e. $R'$=H, $R''$=acyl, i2 e. $R''$=$COR'''$ wherein $R'''$=H, $C_1$–$C_{18}$ alkyl atoms, $C_6$ cycloalkyl atoms, $C_6$–$C_{12}$ aryl atoms, heteroyl atoms, which represents a heterocyclic compound containing in the ring oxygen, sulfur or nitrogen as heteroatom, R, $R_1$ and $R_2$=H or a protecting group which is easily removed in neutral media, such as is benzyl. The new compounds which contain an (un)substituted amino-group form salts with acids, whereas when R=$R_1$=$R_2$=H salts are formed with bases. Unprotected compounds of the formula (I) in the neutral media occur in the form of zwitter-ion.

BRIEF DESCRIPTION OF DRAWINGS

FIG. 1 represents mean values of the effect of compounds according to the present invention on various cell lines.

New derivatives of ascorbic acid (I) which are object of present invention, can be prepared in several ways from the compounds of the general formula (II)

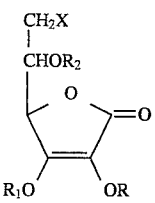
II wherein X=halogen (Cl, Br, J) or amino ($NH_2$). When X=halogen, R =$R_1$=benzyl, $R_2$=H, i.e. R=$R_1$=$R_2$=benzyl, and when X=amino, R=$R_1$=$R_2$=H. New compounds are produced by several types of reactions, illustrated by the following schemes:

1. Reductive alkylation

Reductive alkylation is the treatment of aldehyde or ketone with ammonia or primary, i.e. secondary amines in the presence of hydrogen and a catalyst for hydrogenation. Instead of hydrogen and a catalyst, can be used other reductants, such as borohydrides and formic acid. In the present invention reductive alkylation is carried out with amino-ascorbic acid (II, X=$NH_2$, R=$R_1$=$R_2$=H) with various aldehydes of $R_3CHO$, which is illustrated by the scheme 1:

Scheme 1
Reductive alkylation of amino-ascorbic acid

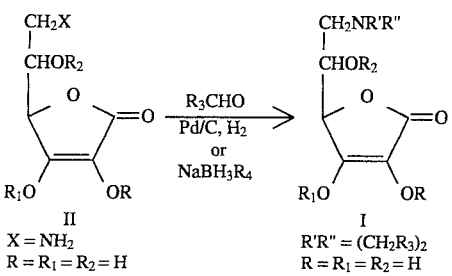

Reductive alkylation is carried out in water as solvent at the temperatures of 20°–25° C. Used reductant is hydrogen with catalyst 5% or 10% Pd/C, or sodium borohydride wherein $R_4$=H or CN. In case catalytic reduction is applied reaction time is 1–2 hours, whereas with borohydrides the reaction takes 5–10 hours. The mechanism of reductive alkylation illustrated by the scheme 1 a Scheme 1a

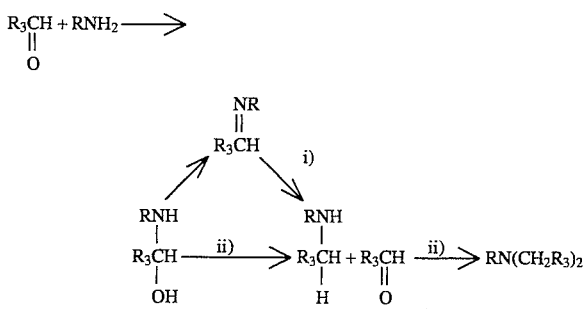

allows obtaining of mono- and disubstituted derivatives of aminoascorbic acid. In our inovation however detected and isolated have been only disubstituted derivatives. This suggests that the reaction of alkylation in the second phase occurs very rapidly.

2. Alkylation reaction

Mono- and disubstituted derivatives of amino-ascorbic acid are prepared by alkylation of corresponding primary and secondary amines, according to the reaction scheme 2.

Scheme 2
Alkylation reaction

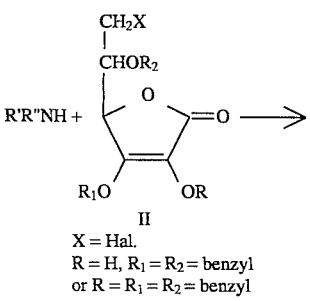

X = Hal.
R = H, $R_1$ = $R_2$ = benzyl
or R = $R_1$ = $R_2$ = benzyl

-continued
Scheme 2
Alkylation reaction

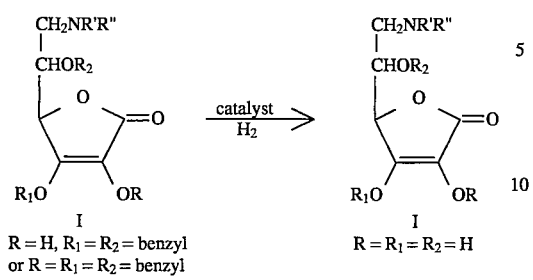

R = H, R$_1$ = R$_2$ = benzyl
or R = R$_1$ = R$_2$ = benzyl

R = R$_1$ = R$_2$ = H

In alkylation reactions are used primary and secondary amines of the general formula NHR'R" wherein R' and R" are as already described for the compounds of the general formula (I). In this reaction the alkylating reagent is halogen-ascorbic acid of the general formula (II). Because halogen-ascorbic acid has three more hydroxy groups of which hydroxy groups of enediol system in the positions C$_2$ and C$_3$ are very reactive in the alkaline medium, it is necessary to protect the molecule adequately prior to the reaction. In other words it is necessary to select protecting groups which are removed in neutral media, such as is benzyl group. The protecting reaction is carried out according to the scheme 2a.

Scheme 2a
Protection of hydroxyl groups of halogen-ascorbic acid

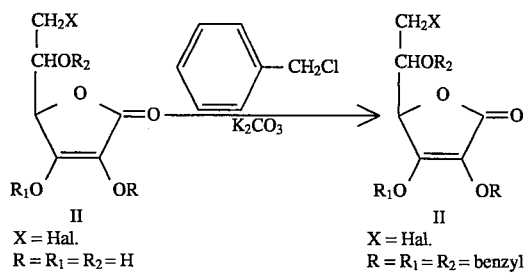

II
X = Hal.
R = R$_1$ = R$_2$ = H

II
X = Hal.
R = R$_1$ = R$_2$ = benzyl

Product of the reaction depends upon molar proportion of the reactants. If for one mole of halogen-ascorbic acid two moles of the protecting reagents are used, produced is the compound of the general formula (II) wherein, R$_2$=H, and if three moles or larger molar excess of this reagent is used, obtained is a fully protected compound. Deprotection of the protecting groups is carried out in the neutral media by catalytic reduction, as is illustrated by the scheme 2. Also the reaction can be carried out without isolation of an intermediate by the addition of a catalyst to the reaction mixture after alkylation is finished, and thereafter by deprotection (one-pot-reaction) under hydrogen atmosphere, wherein it has been noted that in the fully protected compound the protecting group R$_2$ is not easy to deprotect, and therefore in such types of reactions mostly used are the compounds of the general formula (II) wherein R$_2$=H.

3. Acylaton reaction

Acylating reaction of amino- group is carried out by the reagents commonly mentioned in chemical literature, such as are chlorides or anhydrides of acids or active esters of acids i.e. by the reagents of the general formula:

R$_5$COR$_6$ wherein R$_5$=H, alkyl, cycloalkyl, aryl or heteroil having the meaning as described for the formula (I), and R$_6$=Cl, or OCOR$_7$ wherein R$_7$=alkyl, or OR$_8$ wherein R$_8$ is the group known in chemistry as the active ester group, such as are succinyl or benzotriazolyl.

Acylation reaction is illustrated by the scheme 3.

Scheme 3
Acylation of amino- group

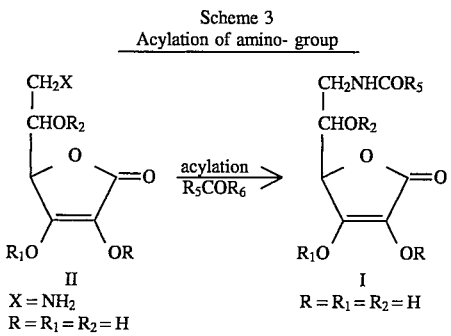

II
X = NH$_2$
R = R$_1$ = R$_2$ = H

I
R = R$_1$ = R$_2$ = H

If the reaction of amine acylation is carried out with formic acid (R$_5$=R$_6$=OH) or with a mixed anhydride of formic and acetic acids (R$_5$=H, R$_6$=OCOR$_7$, R$_7$=CH$_3$), resulting is N-formyl derivative. It is a known fact that under the reductive conditions N-formyl derivatives can be converted to the corresponding monomethyl amino-derivatives. Amino-ascorbic acid however has shown to produce acyl derivatives which are very stable under reductive conditions. For example formyl amino-ascorbic acid is not reduced at the pressure of 80 bar and at 80° C. and acyl derivatives of amino-ascorbic acid are far more stabile at high temperatures than ascorbic acid. Under mentioned conditions maintained over 8 hours chromatography cannot record any disintegration of the molecule. As the derivatives of acylamino-ascorbic acid retain their reducing property they can be used as antioxidants at the temperatures exceeding that for ascorbic acid.

New derivatives of amino-ascorbic acid demonstrate anticarcinogenic properties which have been tested on the following lines of tumor cells: HeLa (carcinoma of the portio vaginalis cervicis); Hep 2 (carcinoma of the larynx); MiaPaCa 2 (carcinoma of the pancreas) and K562 (erythroleukemia), all human cell lines and W138 (normal human fibroblasts) which are used as the control.

Cell lines of human tumors and human fibroblasts are grown on the liquid DMEM media (Dulbecco's modified Eagle's medium) with the addition of 10% of the calf fetus serum (FCS), 2 mM glutamine, 100 U/ml penicillin and 100 µg/ml streptomycin in the humid atmosphere with 5% CO$_2$ at 37° C. The cells are inoculated in the concentration of 10$^4$ cells/ml.

The samples are dissolved in DMEM without the addition of serum, and 0.1N NaOH is added till pH 7.4. Used concentrations are 10$^{-3}$M, 2×10$^{-3}$M and 3×10$^{-3}$M. The results illustrated in FIG. 1 represent mean values of four parallel samples±standard deviation (SD). The results are illustrated by the FIG. 1.

As can be noted from the FIG. 1 the growth of normal fibroblast W138 cells is not affected by the tested derivatives which do inhibit the growth of tumor cells, especially Hep 2.

Preparation of new derivatives of amino-ascorbic acid is illustrated by the following examples, which do not limit the inovation at any point.

Examples of reductive alkylation

EXAMPLE 1

N,N'-dimethylamino-ascorbic acid
(I, R'=R"=CH$_3$, R=R$_1$=R$_2$=H)

Process a): reduction with the aid of the Pd/C catalyst.

To the solution of amino-ascorbic acid (II, X=$NH_2$, R=$R_1$=$R_2$=H)(1.2 g) in water (100 ml) 35% water solution of formaldehyde (2.4 ml) and catalyst 10% Pd/C (0.48 g) are added, whereafter stirred at hydrogen pressure of 0.8 bar in the bottle according to Parr for 1 hour. Catalyst is removed by filtration, and water solution evaporated to the volume of approximately 2–3 ml. The concentrate is purified by column chromatography on silica gel (Kieselgel 60 0.063–0.2 mm art. 7734), by elution with the solvent methanol-water= 7:3. Fractions which contain the product (tlc, silica gel 60 $F_{254}$ Merck, detection spraying with phosphoromolybdenic acid) are combined, and thereafter evaporated to dryness to yield 0.3 g of the product, m.p. 207°–210° C.;=$[a]_D^{20}$=+46.5° (c=0.1 $H_2O$).

IR (KBr)($cm^{-1}$): 3400, 2900, 2800, 2350, 1750, 1650, 1620, 1480, 1430, 1100, 1050.

$^1$H NMR ppm (d) ($D_2O$): 2.83 (6H, s), 3.22–3.37 (2H, m) 4.2–4.25 (1H, m), 4.28–4.29) (1H, d, J=2.17 Hz).

$^1$H NMR ppm (d) ($CF_3COOD$): 3.2–3.23 (6H, d, J=8.79 Hz), 3.58–3.83 (2H, m), 4.79–4.83 (1H, m), 5.02 (1H, s).

$^{13}$C NMR ppm (d) ($CF_3COOD$+$D_2O$): 40.97, 44.19, 58.47, 62.98, 75.43, 152.43, 161.23.

EI-MS m/s: 203 (M+), 58, 82, 88, 112, 130.

EXAMPLE 2

Process b): reduction with borohydride

To the solution of amino-ascorbic acid (0.5 g) in water (50 ml) 35% water solution of formaldehyde (1 ml), sodium cyanoborohydride ($NaBH_3CN$, 0.537 g) and cold acetic acid (0.3 g) are added, thereafter stirred in nitrogen atmosphere for 5 hours at 20°–25° C. The reaction mixture is then concentrated to the volume of approximately 1–2 ml, purified by column chromatography on silica gel, and thereafter eluted with solvent methanol-water=7:3. Fractions which contain the product (tlc) are combined, and thereafter evaporated to dryness to yield 0.28 g of the product identical with that from Example 1.

EXAMPLE 3

N,N'-di-n-propylamino-ascorbic acid
(I, R'=R"=$C_3H_7$, R=$R_1$=$R_2$=H)

To the solution of amino-ascorbic acid (0.32 g) in water (15 ml) n-propanol propanol ($C_3H_6O$, 0.11 g), sodium cyanoborohydride ($NaBH_3CN$, 0.32 g), and thereafter cold acetic acid (0.2 ml) are added, whereafter the reaction mixture is stirred in nitrogen atmosphere for 3 hours at 20°–25° C. The reaction mixture is concentrated to the volume of approximately 1 ml, and purified by column chromatography on silica gel, by elution with solvent ethanol-water=1:1. Fractions which contain the product (tlc, silica gel 60 $F_{254}$, EtOH:$H_2O$=9:1) are evaporated to dryness to yield 0.2 g of the product.

$^1$NMR ppm (d) ($D_2O$): 0.9–0.94 (6H, t) 1.69–1.7 (4H, m), 3.11–3.2 (4H, t), 3.37–3.38 (2H, m), 3.4–3.45 (1H, m), 4.37–4.38 (1H, d).

EXAMPLE 4

N,N'-dibenzylamino-ascorbic acid
(I, R'=R"=$CH_2C_6H_5$, R=$R_1$=$R_2$=H)

To the solution of amino-ascorbic acid (0.36 g) in water (20 ml) benzaldehyde (0.228 g), sodium cyanoborohydride (0.382 g) and cold acetic acid (0.2 ml) are added, thereafter stirred in nitrogen atmosphere for 3 hours at 20°–25° C. The reaction mixture is concentrated to the volume of approximately 1 ml, and purified by column chromatography on silica gel (Kieselgel 60 0.063–0.2 mm art. 7734), by elution with solvent ethanol-water=8:2. Fractions which contain the product (tlc) are combined, and thereafter evaporated to dryness to yield 0.25 g of the product.

$^1$H NMR ppm (d) ($D_2O$): 3.92 (2H, s), 4.31–4.35 (1H, m), 4.59–4.61 (1H, d, J=2.15 Hz), 4.83 (4H, s), 7.59–7.69 (10H, m).

EXAMPLE 5

N,N'-difurfurylamino-ascorbic acid
(I, R'=R"=$CH_2C_4H_3O$, R=$R_1$=$R_2$=H)

To the solution of amino-ascorbic acid (0.52 g) in water (26 ml) furfural (1.45 g), sodium cyanoborohydride (0.565 g) and cold acetic acid (0.5 ml) are added, whereafter the reaction mixture is mixed in nitrogen atmosphere for 5 hours at 20°–25° C. The mixture is concentrated at reduced pressure to the volume of 2 ml, and purified by column chromatography on silica gel, by elution with solvent ethanol-water=8:2. Fractions which contain the product (tlc) are combined, and thereafter evaporated to dryness to yield 0.7 g of the product.

mp=220° C. (decomposition):=$[a]_D^{20}$=+22° (c=0.58 $H_2O$). IR (KBr) ($cm^{-1}$): 3550, 3500, 3450, 2350, 2200, 1630, 1380, 1100, 750.

Examples of alkylating reactions

EXAMPLE 6

N-methylamino-ascorbic acid
(I, R'=H, R"=$CH_3$, R=$R_1$=$R_2$=H)

To the solution of 2,3-dibenzyl-6-bromo-6-deoxy-ascorbic acid (II, X=Br, R=$R_1$=Bn, $R_2$=H) (0.5 g) in methanol (10 ml), 20% methanol solution of methylamine (10 ml) is added and stirred for 1 hour, whereafter it is allowed to stand overnight at 20° C. The reaction mixture is concentrated at reduced pressure to dryness. To the residue methanol (15 ml) and catalyst 10% Pd/C (0.015 g) are added and stirred at hydrogen pressure of 2 bar in the bottle according to Parr for 3 hours. Catalyst is separated by filtration, thereafter the solution concentrated at reduced pressure to the volume of 2 ml, and then purified by column chromatography on silica gel, by elution with solvent methanol-water 8:2. Fractions which contain the product (tlc) are combined, and thereafter evaporated to dryness to yield 0.05 g of the product.

mp=155°–160° C.; IR (KBr) ($cm^{-1}$): 3400, 2900, 2810, 2380, 1740, 1600, 1480, 1380, 1150, 1110, 1050.

$^1$H NMR ppm (d) ($D_2O$): 2.72 (3H, s), 3.21–3.29 (2H, m), 3.73–4.29 (1H, m), 4.37–4.40 (1H, d, J=2.2 Hz).

EXAMPLE 7

N,N'-dimethylamino-ascorbic acid
(I, R'=R"=$CH_3$, R=$R_1$=$R_2$=H)

To the solution of 2,3-dibenzyl-6-bromo-6-deoxy-ascorbic acid (II, X=Br, R=$R_1$=Bn, $R_2$=H) (0.27 g) in methanol (5 ml), 20% methanol solution of dimethylamine (5 ml)is added, stirred for 1 hour, and thereafter allowed to stand for 24 hours at 20°–25° C. The reaction mixture is concentrated at reduced pressure to dryness. The residue is dissolved in methanol (10 ml) wherein 10% Pd/C as a catalyst (0.01 g) is added and stirred at hydrogen pressure of 2 bar in the bottle according to Parr for 3 hours. Catalyst is separated by filtration, and methanol concentrated at reduced pressure to the volume of 2 ml. Thereafter it is purified by column chromatography on silica gel, by elution with solvent methanol-water 8:2. Fractions which contain the product (talc) are combined, and thereafter evaporated to dryness to yield 0.03 g of the product which is identical with that from the Example 1.

Protection of hydroxy groups of halogen-ascorbic acid

EXAMPLE 8

2,3,5-tribenzyl-6-bromo-6-deoxy-ascorbic acid
(II, X=Br, R=$R_1$=$R_2$=Bn)

To the solution of 6-bromo-6-deoxy-ascorbic acid (II, X=Br, R=$R_1$=$R_2$=H) (1 g) in dimethylformamide (15 ml), potassium carbonate (0.91 g) and benzylchloride (1.64 g) are added, and thereafter stirred in nitrogen atmosphere for 2 hours at 60° C. The reaction mixture is concentrated at reduced pressure to dryness, whereafter to the residue chloroform (15 ml) and water (5 ml) are added. Organic layer is separated and washed twice with water (5 ml), and thereafter dried over sodium sulfate sicc. Chloroform solution is concentrated at reduced pressure to the volume of 2 ml, whereafter it is purified by column chromatography on silica gel, by elution with solvent chloroform-ethanol 32:1. Fractions which contain the product are combined, and thereafter evaporated to dryness to yield 0.2 g of the product.

IR $CHCl_3$ ($cm^{-1}$): 3400, 3090, 3060, 3040, 2950, 1760, 1670, 1500, 1460, 1320, 1210, 1150, 1050.

$^1$H NMR ppm (d) ($CDCl_3$): 3.51–3.54 (2H, m), 4.03–4.07 (1H, m), 4.91–4.92 (1H, d, J=2.14 Hz), 5.08 (2H, s), 5.09 (2H, s), 5.16–5.19 (2H, d), 7.20–7.37 (15 H, m).

EXAMPLE 9

Process for the preparation of 2,3-dibenzyl-6-bromo-6-deoxy-ascrobic acid
(II, X=Br, R=$R_1$=Bn, $R_2$=H)

To the solution of 6-bromo-6-deoxy-ascorbic acid (II, X=Br, R=$R_1$=$R_2$=H) (2 g) in dimethylformamide (30 ml) potassium carbonate (1.2 g) and benzyl chloride (2.2 g) are added, whereafter stirred in nitrogen atmosphere for 2 hours at 60° C. Reaction mixture is concentrated at reduced pressure to oily residue. To the residue chloroform (30 ml) and water (10 ml) are added. Organic layer is separated and washed with water (2×10 ml), and then dried over sodium sulfate ;sicc. The solution of chloroform is concentrated to the volume of 2 ml, whereafter it is purified by column chromatography on silica gel, by elution with solvent methylene chloride-ethanol (80:1). Fractions which contain the product (tlc) are combined, and thereafter evaporated to oily precipitate which has all physico-chemical properties described in the literature[1].

Acylation reaction

References Cited: [1]Von F. Dallacker and J. Sanders Chem.-Zeitung. 109 (1985) 277–280.

EXAMPLE 10

Formylamino-ascorbic acid
(I, R'=H, R"=CHO, R=$R_1$=$R_2$=H)

Anhydride of acetic and formic acid (3.7 ml) is prepared by stirring acetic acid anhydride (2.5 ml) and formic acid (1.2 ml) for 2 hours at 50°–60° C. Thereafter it is cooled to 0° C. Amino-ascorbic acid (I, R'=R"=H, R=$R_1$=$R_2$=H, 0.5 g) is dissolved and stirred for 4.5 hours at 20°–24° C. The reation mixture is concentrated at reduced pressure, evaporated after the addition of water (5 ml), and then dissolved in 2 ml water. Thereafter it is purified by column chromatography on silica gel. Next, it is eluted with solvent methanol-acetonitrile 8:2. Fractions which contain the product (tlc) are combined and concentrated to dryness at lower pressure to yield 0.26 of the. product.

mp=200° C. (decompos.) IR (KBr) ($cm^{-1}$): 3450, 2900, 2350, 1740, 1670, 1600, 1390, 1250, 1150, 1110, 1050.

$^1$H NMR ppm (d) ($D_2O$): 3.31–3.54 (2H, m), 3.97–4.02 (1H, m), 4.42 (1H, d, J=2.3 Hz), 8.03 (1H, s).

$^{13}$C NMR ppm (d) ($CF_3COOD+D_2O$): 43.2, 66.0, 78.2, 119.3, 153.8, 166.9, 174.0

El-MS m/s: 55, 56, 57, 59, 62, 69, 70, 73, 84,85, 86, 87, 103, 113.

The solution of amino ascorbic acid (I, R',R"=H, R=$R_1$=$R_2$=H, 0.5 g) in the mixed anhydride of formic and acetic acid (3.7 ml) whic is prepared by stirring acetic acid anhydride (2,5 ml) and formic acid (1.2 ml) for 2 hours at 50°–60° C., followed by cooling at 0° C., is stirred for 4,5 hours at 20°–24° C.

We claim:

1. Derivatives of amino-ascorbic acid of the general formula (1):

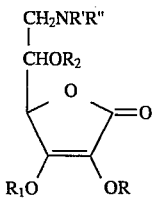

wherein R'=H,R"=COR"" wherein R""=H, $C_1$–$C_{18}$ alkyl, $C_6$ cycloalkyl, $C_6$–$C_{12}$ aryl, or heteroyl atoms, which represents a heterocyclic compound containing in the ring oxygen, sulfur or nitrogen as heteroatom and R, $R_1$ and $R_2$=H or benzyl and their salts with acids and alkalis.

2. Derivative of amino-ascorbic acid of the formula (1) according to claim 1 is characterized by R=$R_1$=$R_2$=H.

3. Derivative of amino-ascorbic acid of the formula (1) according to claim 1 is characterized in that R'=H, R"=formyl and R–$R_1$=$R_2$=H.

4. Derivatives of halogen-ascorbic acid of the general formula (II):

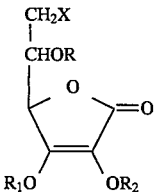

wherein X=chlorine, bromine or iodine and R=$R_1$=$R_2$= benzyl.

5. Derivatives of halogen-ascorbic acid of the general formula (11) is characterized in that X=bromine, R=$R_1$=$R_2$= benzyl.

* * * * *